US006569422B1

(12) United States Patent
van Loon et al.

(10) Patent No.: US 6,569,422 B1
(45) Date of Patent: May 27, 2003

(54) GENETICALLY ENGINEERED CELL CULTURE ADAPTED INFECTIOUS BURSAL DISEASES VIRUS (IBDV) MUTANTS

(75) Inventors: Adriaan Antonius Wilhelmus Maria van Loon, Sambeek (NL); Egbert Mundt, Millienhagen (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/192,469

(22) Filed: Jul. 10, 2002

Related U.S. Application Data

(62) Division of application No. 09/513,487, filed on Feb. 25, 2000, now Pat. No. 6,492,148.

(30) Foreign Application Priority Data

Mar. 5, 1999 (EP) .............................................. 99200647

(51) Int. Cl.[7] .......................... A01N 63/00; A61K 39/12
(52) U.S. Cl. .................. 424/93.2; 424/93.6; 424/205.1; 435/173.3; 435/235.1; 435/236
(58) Field of Search ................................ 424/93.2, 93.6, 424/816, 205.1; 435/173.3, 235.1, 236

(56) References Cited

FOREIGN PATENT DOCUMENTS

| WO | 95 26196 A | 10/1995 |
|---|---|---|
| WO | 98 09646 A | 3/1998 |

OTHER PUBLICATIONS

Lim, B.L.: "Generation of CEF–adapted mutant from a very virulent IBDV strain by reverse genetics: a novel method for development of IBDV vaccine" Proceedings of the 4th Asia Pacific Poultry Health Conference (Nov. 1998) Retrieved from the Internet.

Cao, Y.C. et al: "Molecular characterization of seven chinese isolates of infectious bursal disease virus: classical, very virulent, and variant strains." Avian Diseases vol. 42 (Apr. 1998).

Yamaguchi, T et al: "Identification of sequence changes responsible for attenuation of highly virulent infectious bursal disease virus." Virology vol. 223 (1996).

*Primary Examiner*—Laurie Scheiner
(74) *Attorney, Agent, or Firm*—William P. Ramey, III

(57) ABSTRACT

The present invention relates to a method for the adaptation of infectious bursal disease viruses (IBDV) to growth in CEF cell culture. Changing the codons for amino acid residues 253 (Gln) and 284 (Ala) to 253 (His) and 284 (Thr) allowed bursa adapted Classical and Variant-E IBDV to grow in CEF cell culture. For GLS IBDV only a change of the codon for amino acid residue 284 was necessary.

9 Claims, 9 Drawing Sheets

Figure 1A:
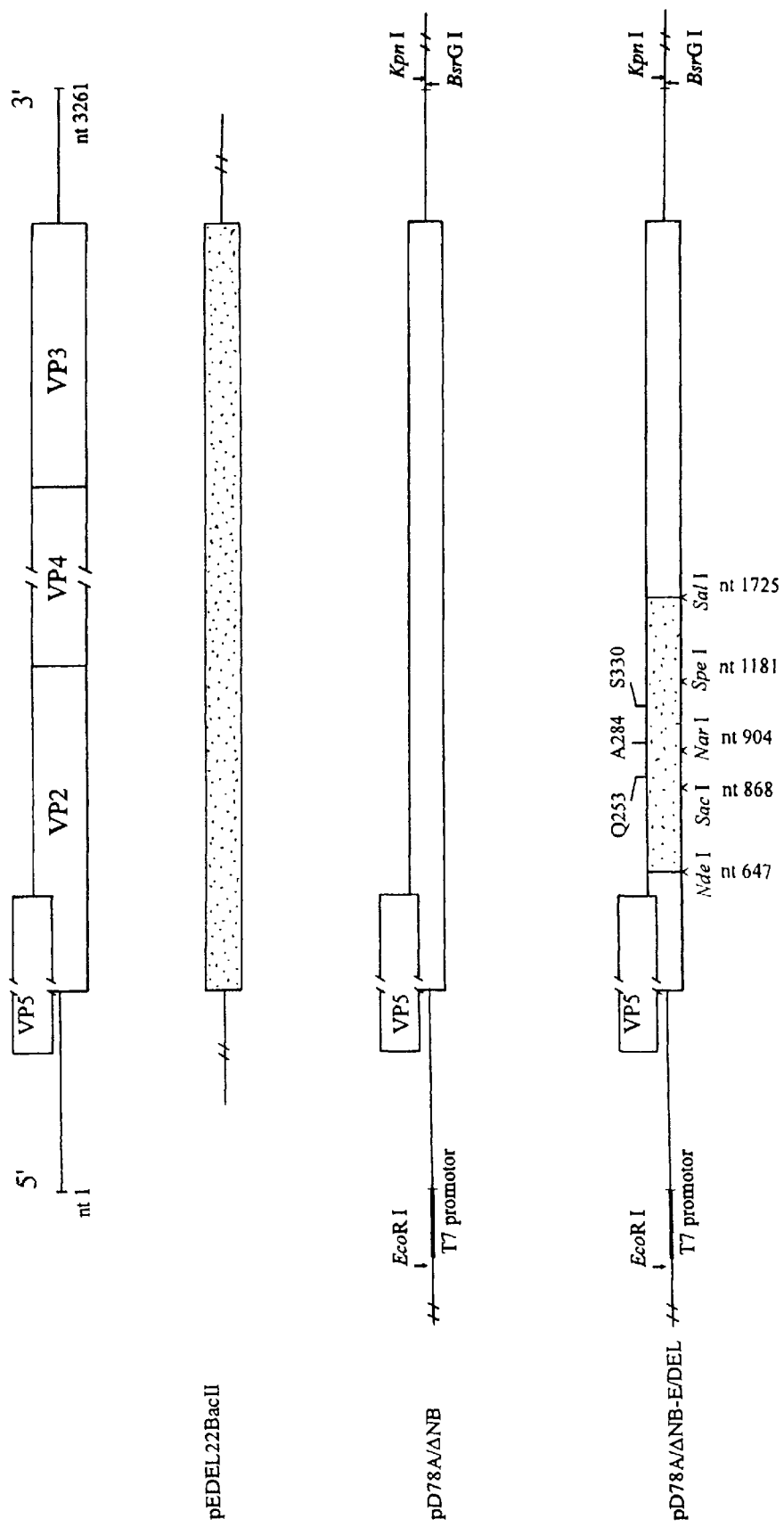

SEQUENCE LISTING

<160> NUMBER OF SEQ ID NOS: 9

<210> SEQ ID NO 1
<211> LENGTH: 25
<212> TYPE: DNA
<213> ORGANISM: infectious bursal disease virus

<400> SEQUENCE: 1
gatcagctcg aagttgctca cccca                                          25

<210> SEQ ID NO 2
<211> LENGTH: 24
<212> TYPE: DNA
<213> ORGANISM: infectious bursal disease virus

<400> SEQUENCE: 2
caagcctcag cgttgggggga gagc                                          24

<210> SEQ ID NO 3
<211> LENGTH: 99
<212> TYPE: DNA
<213> ORGANISM: infectious bursal disease virus

<400> SEQUENCE: 3
gggcgccacc atctacctta taggctttga tgggactgcg gtaatcacca gagctgtggc    60
cgcaaacaat gggctgacga ccggcatcga caatcttat                           99

<210> SEQ ID NO 4
<211> LENGTH: 31
<212> TYPE: DNA
<213> ORGANISM: infectious bursal disease virus

<400> SEQUENCE: 4
gagagctcgt gtttcaaaca agcgtccaag g                                   31

<210> SEQ ID NO 5
<211> LENGTH: 22
<212> TYPE: DNA
<213> ORGANISM: infectious bursal disease virus

<400> SEQUENCE: 5
cgtcctagta ggggaagggg tc                                             22

<210> SEQ ID NO 6
<211> LENGTH: 31
<212> TYPE: DNA
<213> ORGANISM: infectious bursal disease virus

<400> SEQUENCE: 6
gagagctcgt gttcaaaaca agcgtccata g                                   31

<210> SEQ ID NO 7
<211> LENGTH: 56
<212> TYPE: DNA
<213> ORGANISM: infectious bursal disease virus

<400> SEQUENCE: 7
cggagggccc ctggatagtt gccaccatgg atcgtcactg ctaggctccc acttgc        56

<210> SEQ ID NO 8
<211> LENGTH: 100

-continued

```
<212> TYPE: DNA
<213> ORGANISM: infectious bursal disease virus

<400> SEQUENCE: 8
cgtaggctac tagtgtgacg ggacggaggg ctcctggata gttgccacca tggatcgtca      60
ctgctaggct ccccgtgcc gaccatgaca tctgttcccc                            100

<210> SEQ ID NO 9
<211> LENGTH: 100
<212> TYPE: DNA
<213> ORGANISM: infectious bursal disease virus

<400> SEQUENCE: 9
gggcgccacc atctacctca taggctttga tgggacaacg gtaatcacca gggctgtggc      60
cgcaaacaat gggctgacgg ccggcaccga caaccttatg                           100
```

GENETICALLY ENGINEERED CELL CULTURE ADAPTED INFECTIOUS BURSAL DISEASES VIRUS (IBDV) MUTANTS

The present application is a divisional of U.S. application Ser. No. 09/513,487 filed on Feb. 25, 2000, now U.S. Pat. No. 6,492,148.

The present invention is concerned with a method for the preparation of an infectious IBDV mutant capable of replication in CEF cell culture, a genetically engineered IBDV mutant as well as with a vaccine comprising such a IBDV mutant.

Infectious bursal disease virus (IBDV) is a member of the Birnaviridae family. Viruses in this family have a very similar genomic organisation and a similar replication cycle. The genomes of these viruses consist of 2 segments (A and B) of double-stranded (ds) RNA. The larger segment A encodes a polyprotein which is cleaved by autoproteolysis to form mature viral proteins VP2, VP3 and VP4. VP2 and VP3 are the major structural proteins of the virion. VP2 is the major host-protective immunogen of birnaviruses, and contains the antigenic regions responsible for the induction of neutralising antibodies. The VP4 protein appears to be a virus-coded protease that is involved in the processing of a precursor polyprotein of the VP2, VP3 and VP4 proteins. The larger segment A possesses also a second open reading frame (ORF), preceding and partially overlapping the polyprotein gene. This second open reading frame encodes a protein VP5 of unknown function that is present in IBDV infected cells. The smaller segment B encodes VP1, a 90 kDa multifunctional protein with polymerase and capping enzyme activities.

For IBDV, two serotypes exist, serotype 1 and 2. The two serotypes may be differentiated by virus neutralisation (VN) tests. Furthermore, subtypes of serotype 1 have been isolated. These so-called "variant" viruses of serotype 1 can be identified by cross-neutralisation tests, a panel of monoclonal antibodies or RT-PCR. These subtypes of serotype 1 of IBDV have also been described in literature, for example: classical, variant-E, GLS, RS593 and DS326 strains (Van Loon, et al. Proceedings of the International symposium on infectious bursal disease and chicken infectious anaemia, Rauischholzhausen, Germany, 179–187, 1994).

Infectious Bursal disease (IBD), also called Gumboro disease, is an acute, highly-contagious viral infection in chickens that has lymphoid tissue as its primary target with a selective tropism for cells of the bursa of Fabricius. The morbidity rate in susceptible flocks is high, with rapid weight loss and moderate mortality rates. Chicks that recover from the disease may have immune deficiencies because of the destruction of the bursa of Fabricius which is essential to the defence mechanism of the chicken. The IBD-virus causes severe immunosuppression in chickens younger than 3 weeks of age and induces bursal lesions in chicks up to 3 months old.

For many years the disease could be prevented by inducing high levels of antibodies in breeder flocks by the application of an inactivated vaccine, to chickens that had been primed with attenuated live IBDV vaccine. This has kept economic losses caused by IBD to a minimum. Maternal antibodies in chickens derived from vaccinated breeders prevents early infection with IBDV and diminishes problems associated with immunosuppression. In addition, attenuated live vaccines have also been used successfully in commercial chicken flocks after maternal antibodies had declined.

Recently, very virulent strains of IBDV have caused outbreaks of disease with high mortality in Europe. The current vaccination programs failed to protect chicks sufficiently. Vaccination failures were mainly due to the inability of live vaccines to infect the birds before challenge with virulent field virus.

Therefore, a constant need exists to improve existing vaccines and to develop new types of vaccines. For the development of live vaccines IBD viruses in attenuated form are required. Conventionally, this can be achieved by serial passaging of IBDV field isolates on an appropriate substrate. For the development of inactivated IBDV vaccines, an appropriate substrate is necessary for the generation of high amounts of IBDV antigen mass resulting from the propagation of IBD viruses on the substrate.

It is known that field IBDVs can readily be propagated in vivo in the bursa of infected birds or in embryonated eggs. However, although, the successful adaptation an propagation of some IBDV strains to in vitro cell culture of chicken embryo origin has been reported, it is generally acknowledged that most IBDV strains isolated from infected bursa in the field, in particular the so-called virulent- or very virulent IBDV strains cannot be adapted to cells of chicken embryo origin, such as chicken embryo fibroblasts (CEF) or cells from other organs such as the kidney and liver (Brown et al., J. Gen. Virology 75, 675–680, 1994; van Loon, et al., 1994, supra).

The drawbacks of the in vivo culture substrates are obvious. Such culture methods are animal unfriendly, need a lot of animals, are time consuming and cannot be carried out under standardised and stringent conditions.

In addition, the limited number of IBDV strains which are not refractory to adaptation to in vitro cell culture substrates, suffer from the disadvantage that as a result of the serial passaging process leading to the adaptation of the IBDV strains, random mutations are introduced in the genome of the virus in an uncontrolled manner. Such mutations may influence properties of the virus other than that associated with the adaptation of the virus to the cell culture, e.g. properties related to the immunogenicity of the virus. Such additional, random mutations are not desired. The adaptation of the IBDVs by passaging of the virus in vitro in CEF cell cultures has been associated with attenuation of the virulence as demonstrated by a reduction of the virus' ability to induce lesions in the bursa of the infected bird. Yamaguchi et al. (Virology 223, 219–223, 1996) investigated the molecular basis for the virulence of IBD viruses and the attenuation of these viruses as a result of the adaptation of bursa IBDVs to CEF cell culture. It was concluded that from the studies carried out by Yamaguchi et al. the precise mutations involved in attenuation of the wild-type IBDV could not be identified. It was suggested that the amino acid residues at position 279 (Asp/Asn) and 284 (Ala/Thr) of the polyprotein encoded by the long open reading frame of the segment A are important for virulence or propagation of the IBDV in CEF cells.

The latter was confirmed by Lim, B-L (Proceedings of the 4th Asia Pacific Poultry Health Conference, Nov. 22–26, 1998, Melbourne, Australia, Abst. 79). It is disclosed therein that substitution of the amino acid residues 279 (Asp→Asn) and 284 (Ala→Thr) in the VP2 protein of an IBDV results in a IBDV mutant which can be propagated in CEF cell culture. However, the prior art does not teach an alternative of type and minimal number of amino acid mutations which are required and sufficient to allow the adaptation of bursa IBDV to CEF cell culture.

It is an object of this invention to provide a generally applicable method for adaptation of IBDV isolates which only grow in vivo in the bursa of infected birds to growth in cell culture.

It is a further object of the present invention to provide a method for preparing attenuated IBDV mutants by introducing mutations in the IBDV genome in a controlled manner.

Moreover, it is an object of the present invention to provide a genetically engineered IBDV mutant comprising the appropriate amino acid residues which allow the mutant to grow in cell culture.

It has been found that this object has been met by a method for the preparation of an infectious IBDV mutant capable of replication in CEF cell culture comprising the steps of, (i) separately preparing a DNA construct comprising cDNA of genome segments
A and B of an IBDV not capable of replication in CEF cell culture,
  (ii) introducing a mutation in:
    a one or more codons for amino acid residues 253 and 284 of the VP2 gene of Variant-E or Classical IBDV strains, or in
    b a codon for amino acid residue 284 of the VP2 gene of a GLS IBDV strain, on the cDNA comprising the segment A, such that the codons for amino acid residues 253 and 284 of the mutated VP2 gene encode a histidine and threonine residue, respectively, in the case of a Variant-E or Classical IBDV strain, or such that the codon for amino acid residue 284 of the mutated VP2 gene encodes a threonine residue in the case of a GLS IBDV strain,
  (iii) allowing RNA transcripts of the cDNA comprising the segment A and the segment B to initiate replication of the IBDV mutant in host cells in a culture medium, and
  (iv) isolating the IBDV mutant from the culture.

The present invention for the first time identifies which amino acid residues are required and sufficient to allow an IBDV to replicate in CEF cell culture. Whereas most IBDV bursa-isolates comprise the amino acid residues 253 (Gln), 284 (Ala) and 330 (Ser) of the VP2 protein, Variant-E or Classical IBDV mutants whose codons at position 253 and 284 have been changed such that they now encode the amino acid residues 253 (His) and 284 (Thr) are able to grow in CEF cell culture.

For GLS IBDV mutants it has been found that it is sufficient to change the codon at position 284 such that it now encodes the amino acid residue 284 (Thr).

It has also been found that the amino acid position 330 is not critical for the replication of the Classical or Variant-E IBDV mutant in CEF. However, serine, arginine or lysine residues are most favoured at that position in the present invention.

Additionally, it has been found that for GLS IBDV amino acid position 253 is not critical for replication, and usually is a glutamine residue.

Hence, in a preferred method an IBDV mutant is prepared which comprises any of these three amino acid residues, in particular 330 (Arg), at this position in the VP2 protein. For GLS IBDV mutants the preferred amino acid residue at position 253 is a glutamine.

TABLE 1

| IBDV | Amino acid changes | | | CEF growth |
|---|---|---|---|---|
| | 253 | 284 | 330 | |
| D78/Variant-E parent | Gln | Ala | Ser | − |
| mutant | His | Ala | Ser | − |

TABLE 1-continued

| IBDV | Amino acid changes | | | CEF growth |
|---|---|---|---|---|
| | 253 | 284 | 330 | |
| mutant | Gln | Thr | Ser | − |
| mutant | Gln | Ala | Arg | − |
| mutant | His | Thr | Ser | + |
| mutant | Gln | Thr | Arg | − |
| mutant | His | Ala | Arg | − |
| mutant | His | Thr | Arg | + |

It has been found that in the genome of a (chimeric) Variant-E IBDV which was able to replicate only in the bursa of infected chickens (D78/Variant-E), two changes are necessary to adapt IBDV isolates to CEF cell culture. These positions involve amino acid residue 253 and 284. Amino acid residues histidine and threonine at these positions, respectively, allow the IBDV mutant to replicate in CEF cell culture. (Table 1 and Example 1). Furthermore, it has been found that the IBDV mutants adapted to CEF cell culture according to the method of the invention are also attenuated (Example 2).

To further proof that the adaptation from bursa to CEF cells for Classical IBDV strains is also determined by the two amino acids, the codons of IBDV strain D78 which is able to replicate in CEF cell culture were changed at positions 253, 284 and 330. The results are shown in Table 2A.

TABLE 2A

| IBDV | Amino acid changes | | | CEF Growth |
|---|---|---|---|---|
| | 253 | 284 | 330 | |
| D78 parent | His | Thr | Arg | + |
| Mutant | Gln | Thr | Arg | − |
| Mutant | His | Ala | Arg | − |
| Mutant | His | Thr | Ser | + |
| Mutant | Gln | Ala | Ser | − |

Classical "very virulent" (VV) European isolate UK661 (Brown et al., J. Gen. Virology 75, 675–680, 1994; Brown and Skinner, Virus Res. 40, 1–15, 1996) cannot be propagated in vitro, and therefore has to be propagated in vivo in chickens. Chickens have to be infected with the VV strain and a few days post-infection surviving birds are killed and the bursa is removed. The virus can then be extracted from bursal homogenate for further use. The experiments underlying the present invention demonstrated that the amino acid changes at positions 253 and 284 as defined above allow the VV strain UK661 to growth in cell culture. The results of the mutagenesis and transfection experiments with this Classical IBDV strain are summarised in Table 2B.

TABLE 2B

| IBDV | Amino acid changes | | | CEF Growth |
|---|---|---|---|---|
| | 253 | 279 | 284 | |
| D78/661 parent | Gln | Asp | Ala | − |
| mutant | Gln | Asn | Thr | +* |
| mutant | His | Asp | Ala | − |
| mutant | Gln | Asp | Thr | − |
| mutant | His | Asp | Thr | + |

*replicates very slow

These data further proof that the amino acid changes at positions 253 and 284 are sufficient to allow Classical bursa IBDV strains to growth in cell culture. All other mutations result in mutants which either do not replicate in cell culture or replicate very poorly (see also Lim et al., J. Virol. 73, 2854–62, 1999).

Additionally, it was determined that in GLS IBDV the exchange of a single amino acid residue at position 284 was sufficient to allow a bursa adapted IBDV to replicate on CEF cells (Table 3).

TABLE 3

| IBDV | Amino acid changes | | | CEF |
|---|---|---|---|---|
| | 253 | 284 | 330 | Growth |
| D78/GLS-BU | Gln | Ala | Ser | − |
| D78/GL-CEF | Gln | Thr | Ser | + |

Therefore, the method according to the invention allows the adaptation of IBDV bursa-isolates to growth in cell culture by means of recombinant DNA techniques. The advantage of the present method is that as a result of the adaptation process only mutations are introduced in the genome of the IBDV in one or more of the codons at position 253 and 284. The numbers indicate the amino acid and codon positions of the polyprotein and large open reading frame on segment A of the IBDV genome, respectively (Mundt and Müller, J. Gen. Virol. 77, 437–443, 1995; NCBI accession number X 84034).

Most but not all IBDV strains which fail to grow on CEF cell culture contain the codons 253 (Gln), 284 (Ala) and 330 (Ser) in the VP2 gene. Some Variant-E or Classical IBDV strains which fail to grow on CEF cell culture may already have one of the required codons 253 (His) and 284 (Thr). Therefore, the method according to the invention comprises the introduction of a mutation in one or two of the required codons mentioned above, such that the resulting IBDV mutant comprises the codons in the VP2 gene encoding the amino acid residues 253 (His) and 284 (Thr).

More preferably, the method of the invention is applied to an IBDV which is not capable of replication in CEF cells and which comprises the codons for amino acid residues 253 (Gln) and 284 (Ala), and even more preferably 330 (Ser). In the case of Classical and Variant-E strains, mutations are introduced in the two or three of the codons of the VP2 gene resulting in the codons 253 (His) and 284 (Thr), and optionally 330 (Arg). The new codons for the amino acids at these positions may be: for His (CAT or CAC), for Thr (ACT, ACC, ACA, ACG) and for Arg (CGT, CGC, CGA, CGG, AGA, AGG).

Even more preferably, the method of the invention is applied to an IBDV which is not capable of replication in CEF cells and which comprises the codons Gln 253 (CAA), Ala 284 (GCC) and optionally Ser 330 (AGT) or any combination thereof.

In particular, the method of the invention is applied to an IBDV which is not capable of replication in CEF cells and which comprises the codons 253 (CAA), 284 (GCC) and 330 (AGT).

The method for the preparation of an IBDV mutant according to the present invention comprises the recently established "reverse genetics" system for birnaviruses (Mundt and Vakharia, Proc. Natl. Acad. Sci. USA 93, 11131–11136, 1996 and WO 98/09646). This reverse genetics system opened the possibility to introduce mutations in the RNA genome of an IBD virus. The principle of the reverse genetics method according to the invention is that genomic RNA segments A and B are isolated from the virus, followed by reverse transcription of the RNAs into cDNA, after which the cDNAs are transcribed into RNA. The introduction of the required mutation(s) into the segment A (or B) of the virus takes place at the cDNA level. An important step in this reverse genetics system is to provide separate DNA constructs comprising a DNA vector molecule (e.g. a plasmid) and full length cDNA clones of the segments A or B of the IBDV. DNA constructs comprising the segment A or B cDNA, including the nucleotides of the 5'- and 3'-ends of both these segments can be generated according to the method described by Mundt and Vakharia (1996, supra). The subsequent step in the reverse genetics method is the transfection of suitable host cells with appropriate segment A and B genetic material such that in the transfected host cells RNA transcripts of cDNA segment A and B can initiate replication of the virus, resulting in infectious IBDV which can be isolated from the medium in which the host cells are cultured.

Several methods for the latter step of the reverse genetics system may be used. Preferably, the method according to the invention comprises the preparation of synthetic RNA transcripts from both the segment A and B cDNAs in vitro. In this case the DNA constructs comprise a RNA polymerase promoter operably linked to either of the segments. The promoter can be the promoter for the T7, SP6 or T3 polymerase, the T7 promoter being preferred. The synthetic transcripts of the A and B segment are isolated and used to transfect suitable host cells.

Alternatively, a method is provided in which a cell line is provided comprising host cells capable of expressing a RNA polymerase and which are transformed with a DNA construct comprising cDNA of segment B and a RNA polymerase promoter, such that RNA transcripts of segment B are constitutively expressed. After transfection of such cells with a synthetic RNA transcript of the cDNA comprising mutated segment A, the replication of the IBDV mutant is initiated in the host cells. In particular, host cells may be used which are able to express bacteriophage T7 DNA-dependent RNA polymerase, expressed for example cytoplasmically from recombinant vaccinia virus.

The desired mutations can be introduced into the VP2 gene by means of methods generally known in the art for this purpose. In particular, the mutation(s) are introduced by means of site-directed mutagenesis. Methods for introducing a mutation in the IBDV genome are described herein, but are also generally used in the art (Mundt and Vakharia, 1996, supra; Yao et al., J. Virology 72, 2647–2654, 1998; Mundt et al. European patent application no. 0887,412 and Current Protocols in Molecular Biology, eds.: F. M. Ausubel et al., Wiley N.Y., 1995 edition, pages 8.5.1.–8.5.9.)

The method according to the invention may be applied to all IBDV strains which are not capable of replication in CEF cell culture, and which are of the Classical, Variant-E, or GLS antigenic sub-types of IBDV.

Moreover, the method according to the invention may be applied to all IBDV strains which are not capable of replication in CEF cell culture, independent of the virulence of the strains, and includes very virulent strains (such as CS89 and UK661), virulent strains (such as F52/70 and STC) and vaccine strains (such as 228E and 2512). The IBDV mutants which are adapted to replication in cell culture derived from very virulent- and virulent strains will be less virulent and may be used as live vaccine strains. Alternatively, such IBDV mutants can be propagated conveniently in cell culture and formulated as inactivated vaccines.

The method according to the invention may also be advantageously applied to IBDV attenuated strains which are not capable of replication in CEF cell culture. The mutants derived from such attenuated viruses can be used in a cell culture system for vaccine production in stead of in an in vivo production system.

According to a further aspect, the present invention provides a method for the preparation of a "chimeric" IBDV mutant capable of replication in CEF cell culture. The method comprises the additional step of introducing a mutation in a gene of the segment A, preferably the VP2 gene, of a first IBDV, as a result of which the protein expressed by that gene comprises an epitopic determinant of a second IBDV.

A chimeric IBDV is a virus which comprises as a genetic backbone the segment A or VP2 gene of a first antigenic sub-type, and additionally comprises the genetic information encoding an epitopic determinant of a second IBDV antigenic sub-type. In particular, such chimeric IBDVs express one or more additional epitopic determinants on the VP2 protein of the IBDV of the first antigenic sub-types. The advantage of such a chimeric IBDV is that can be used as a single immunogen which induces immunity against at least two antigenic sub-types of IBDV.

In particular, IBDV mutants are prepared which comprise the segment. A backbone or VP2 gene of Classical, GLS or Variant-E IBDV. cDNA clones containing the entire coding region of the segment A of the various IBDV strains can be prepared using standard cloning procedures and methods described in the prior art (Vakharia et al., Avian Diseases 36, 736–742, 1992; J. Gen. Virology 74, 1201–1206, 1993). The amino acid sequences and nucleotide sequences of the segment A of various IBDV strains are disclosed in the prior art (e.g. WO 95/26196 and Vakharia et al., Avian Diseases 36, 736–742, 1992).

Moreover, WO 95/26196 discloses the amino acid sequence of several epitopic determinants of the IBDV antigenic sub-types which are characteristic for each antigenic subtype In addition, WO 95/26196 discloses the antigenic characterisation of various IBDV strains by their reactivity with a panel of neutralising monoclonal antibodies. Important, epitopic determinants reactive with such neutralising Moabs are the B69 (classic sub-type), R63 and 67 (variant-E) and 57 (GLS) epitopic determinants. The region of the VP2 protein comprising the amino acid sequences for these epitopic determinants are described in Vakharia et al. (Virus Res. 31, 265–273, 1994)

Preferably, in the method according to the present invention a chimeric IBDV mutant capable of replication in CEF cell culture is prepared which comprises a classic segment A backbone and the nucleotide sequence encoding the variant-E epitopic determinant 67, or GLS epitopic determinant 57. Alternatively, the chimeric IBDV mutant comprises a GLS backbone and nucleotide sequences encoding the B69, R63 or 67 epitopic determinant.

In particular, the method according to the invention comprises the preparation of a chimeric IBDV strain (D78/Varaint-E) derived from strain D78 (commercially available from Intervet International B.V., the Netherlands) in which (i) the VP2 gene is replaced by the VP2 gene of a Variant-E strain, and (ii) the codons at positions 253, 284 and 330 are altered as defined-above (Example 1). Basically, the steps for the introduction of nucleotide sequences encoding the epitopic determinants in the backbone segment A of a first IBDV are in essence the same as those for the introduction of the mutations defined-above. This is most easily done by providing cDNA of the genome segments A and B and (i) replacing the coding sequence for the epitopic determinant of the first IBDV by that of the second IBDV, or (ii) altering a specific codon in the first IBDV by site-directed mutagenesis. Such methods are also described in WO 95/26196. Finally, RNA transcripts of these cDNA molecules are allowed to initiate replication in a transfected host cell to obtain infectious, chimeric IBDV.

In another embodiment of the invention a method is provided for the preparation of and IBDV mutant as defined above, wherein the resulting IBDV mutant also comprises other mutations which attenuate the virus. An example of such a mutation is a mutation in the VP5 gene of the segment A of the IBDV genome resulting in an IBDV mutant which is not able to express a native VP5 protein. The preparation of an IBDV VP5$^-$ mutant is described in European patent application No. 887,412.

According to a further aspect, the present invention provides a genetically engineered, infectious IBDV mutant capable of replication in CEF cell culture, comprising codons 253 (His) and 284 (Thr), and optionally 330 (Arg) in the VP2 gene of Classical or Variant-E strains, or codon 284 (Thr) of a GLS strain.

Such IBDV mutants still comprise the genetic information of bursa IBDVs which are not capable of replication in CEF cell culture, with the exception of the new codons mentioned-above which have been introduced in a controlled manner by means of genetic engineering techniques.

In particular, a Variant-E IBDV mutant as defined-above is provided which does not have glycine and/or valine on positions 318 and 325, respectively. Genetically engineered Variant-E mutants having aspartic acid and/or methionine at these positions, respectively, are most preferred.

In a preferred embodiment, the genetically engineered IBDV mutant according to the invention is a chimeric IBDV mutant, in particular a chimeric IBDV mutant derived from strain D78, comprising the nucleotide sequence encoding the VP2 gene of a Variant-E strain and having the three new codons specified above.

The present invention provides the possibility to easily prepare IBDV vaccines from IBDV strains which were previously refractory to replication in vitro cell culture. An additional advantage of the present invention is that IBDVs can be (further) attenuated in a controlled manner by the method described-above. Such attenuated IBDV mutants may be used as the active components in live IBDV vaccines.

Therefore, another aspect of this invention is a vaccine for use in the protection of poultry against disease resulting from IBDV infection. The vaccine comprises a genetically engineered IBDV mutant as prepared above, together with a pharmaceutical acceptable carrier or diluent.

The IBDV mutant can be incorporated into the vaccine as live attenuated or inactivated virus.

A vaccine according to the invention can be prepared by conventional methods such as for example commonly used for the commercially available live- and inactivated IBDV vaccines. Briefly, a susceptible substrate is inoculated with an IBDV mutant according to the invention and propagated until the virus replicated to a desired infectious titre after which IBDV containing material is harvested.

Every substrate which is able to support the replication of IBDV mutants can be used to prepare the vaccine according to the present invention, including primary (avian) cell cultures, such as chicken embryo fibroblast cells (CEF) or chicken embryo liver cells (CEL), mammalian cell lines such as the VERO cell line or the BGM-70 cell line, or avian cell lines such as QT-35, QM-7 or LMH. Usually, after inoculation of the cells, the virus is propagated for 3–10 days, after which the cell culture supernatant is harvested, and if desired filtered or centrifuged in order to remove cell debris.

Alternatively, the IBDV mutant is propagated in embryonated chicken eggs. In particular, the substrate on which these IBDVs are propagated are SPF embryonated eggs. Embryonated eggs can be inoculated with, for example 0.2 ml IBDV mutant containing suspension or homogenate comprising at least $10^2$ $TCID_{50}$ per egg, and subsequently incubated at 37° C. After about 2–5 days the IBD virus product can be harvested by collecting the embryo's and/or the membranes and/or the allantoic fluid followed by appropriate homogenising of this material. The homogenate can be centrifuged thereafter for 10 min at 2500×g followed by filtering the supernatant through a filter (100 µm).

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below.

Although administration by injection, e.g. intramuscular, subcutaneous of the live vaccine according to the present invention is possible, the vaccine is preferably administered by the inexpensive mass application techniques commonly used for IBDV vaccination. For IBDV vaccination these techniques include drinking water and spray vaccination.

Alternative methods for the administration of the live vaccine include in ovo, eye drop and beak dipping administration.

In another aspect of the present invention a vaccine is provided comprising the IBDV mutant in an inactivated form. The major advantage of an inactivated vaccine is the high levels of protective antibodies of long duration that can be achieved.

The aim of inactivation of the viruses harvested after the propagation step is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralised afterwards. Material inactivated with formaldehyde can, for example, be neutralised with thiosulphate. Physical inactivation can preferably be carried out by subjecting the viruses to energy-rich radiation, such as UV light or γ-rays. If desired, after treatment the pH can be adjusted to a value of about 7.

A vaccine containing the inactivated IBDV mutant can, for example comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the IBDV mutant as the active component, i.e. an amount of immunising IBDV material that will induce immunity in the vaccinated birds against challenge by a virulent virus. Immunity is defined herein as the induction of a significant higher level of protection in a population of birds after vaccination compared to an unvaccinated group.

Typically, the live vaccine according to the invention can be administered in a dose of $10^2$–$10^9$ $TCID_{50}$ infectious dose$_{50}$ ($TCID_{50}$) per animal, preferably in a dose ranging from $10^{5.0}$–$10^{7.0}$ $TCID_{50}$, and an inactivated vaccines may contain the antigenic equivalent of $10^5$–$10^9$ $TCID_{50}$ per animal.

Inactivated vaccines are usually administered parenterally, e.g. intramuscularly or subcutaneously.

Although, the IBDV vaccine according to the present invention may be used effectively in chickens, also other poultry such as turkeys, guinea fowl and partridges may be successfully vaccinated with the vaccine. Chickens include broilers, reproduction stock and laying stock.

The age of the animals receiving a live or inactivated vaccine according to the invention is the same as that of the animals receiving the conventional live- or inactivated IBDV vaccines. For example, broilers (free of maternally derived antibodies-MDA) may be vaccinated at one-day-old, whereas broilers with high levels of MDA are preferably vaccinated at 2–3 weeks of age. Laying stock or reproduction stock with low levels of MDA may be vaccinated at 1–10 days of age followed by booster vaccinations with inactivated vaccine on 6–8 and 16–20 weeks of age.

The invention also includes combination vaccines comprising, in addition to the IBDV mutant described above, one or more immunogens derived from other pathogens infectious to poultry or fish, respectively.

Preferably, the combination vaccine additionally comprises one or more vaccine strains of infectious bronchitis virus (IBV), Newcastle disease virus (NDV), egg drop syndrome (EDS) virus, turkey rhinotracheitis virus (TRTV) or reovirus.

EXAMPLES

Example 1

Construction of IBDV Mutants and Their Replication Properties in CEF Cell Culture Material and Methods Construction of (Intergeneric) IBDV Plasmids Comprising the Variable Region of VP2 of Classical, Variant-E or GLS Strains of IBDV (i) VP2 of Classical IBDV Strain D78

A prerequisite for the following site directed mutagenesis was the modification of the plasmid pUC 18. To this end pUC 18 was cleaved with Nde I and BamH I, electroeluted, blunt ended by Klenow enzyme and religated to obtain pUC18 ΔNde I-BamH I (pUC18/ΔNB). Plasmid pAD78/EK (Mundt et al., J. Virology 71, 5647–51, 1997) was cleaved with EcoR I and Kpn I to obtain the full length sequence of segment A of serotype I strain D78 including the T7-RNA polymerase promotor site. This fragment was ligated into the EcoR I and Kpn I cleaved pUC18/ΔNB to obtain pD78A/ΔNB (FIG. 1A). Plasmid pD78A/ΔNB was used as backbone for cloning and site directed mutagenesis procedures.

UK661

Figure 4:
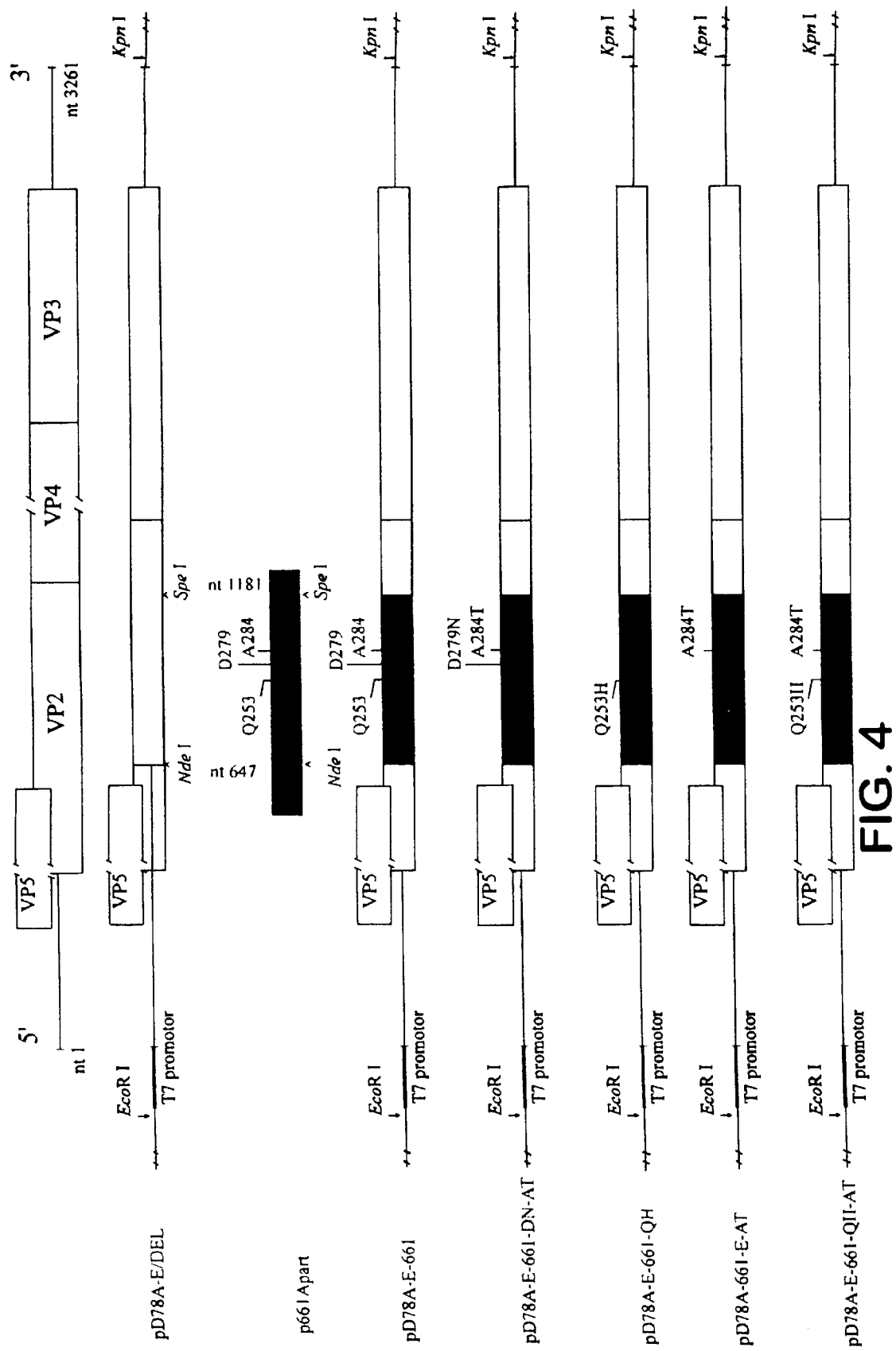

The plasmid pD78-E/DEL (see below) was used for the construction of chimeric plasmids containing sequences of segment A of strain UK 661. After precipitation of viral RNA reverse transcription and PCR were performed following the standard procedures by using oligonucleotides UK661AFor1 and UK661ARev1 (Brown and Skinner, Virus Res. 40, 1–15, 1996, nucleotide no. 621–644-sense- and 1201–1223-antisense, respectively). Resulted PCR fragments were cloned blunt ended into the Sma I-cleaved vector pUC 18 (Pharmacia, Sweden) to obtain p661Apart. After sequencing p661Apart was cleaved with restriction enzymes Nde I and Spe I at nucleotides 647 and 1182, respectively (Numbering follows the full length sequence of strain P2: NCBI accession number X 84034), to obtain a 535 bp fragment encompassing coding sequences of the variable region of VP2 of strain UK661. After ligation into Nde I-Spe I cleaved pD78-E/DEL a chimeric full length plasmid pD78A -E-661 containing sequences of segment A of strain D78, E/Del, and UK661 was established (FIG. 4).

(ii) VP2 of Variant-E IBDV

For substitution of IBDV specific sequences a plasmid containing the complete coding region of the variant E strain E/Del was used (pEDEL22BacII, Vakharia, Biotechnology annual review 3, 151–168, 1997). pEDEL22BacII (FIG. 1A) was cleaved with restriction enzymes Nde I and Sal I, nucleotides 647 and 1725, respectively, in accordance to the full length sequence of strain P2 (NCBI accession number X 84034) to obtain a 1078 bp fragment encompassing coding sequences of the variable region of VP2 and sequences of VP4 of strain E/Del. After ligation into Nde I-Sal I cleaved pD78A/ΔNB a chimeric full length plasmid pD78A/ΔNB-E/Del (FIG. 1A) containing sequences of segment A of strain D78 as well as E/Del was established. Plasmids pAD78/ΔNB and pD78A/ΔNB-E/Del were used for site directed mutagenesis.

(iii) VP2 of GLS IBDV

Figure 1B:
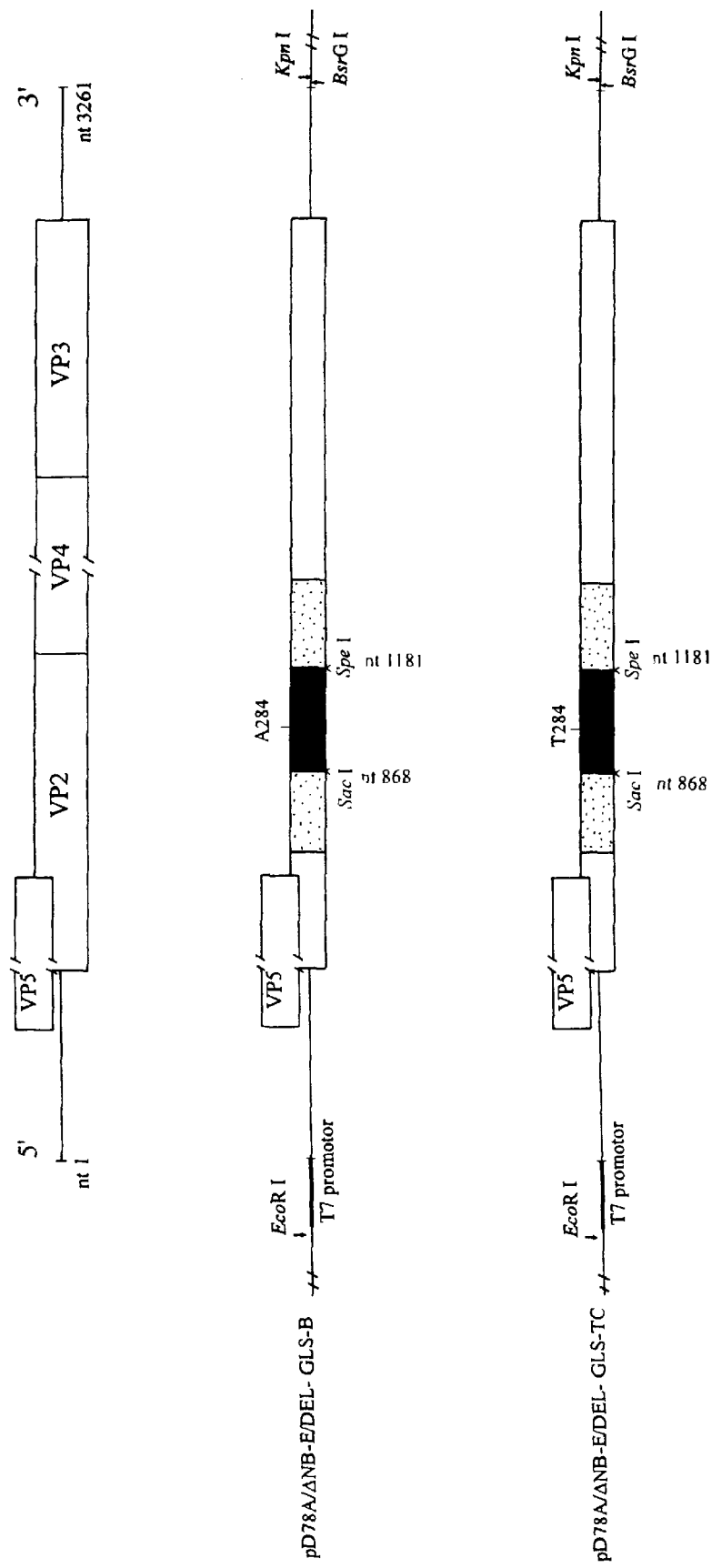

Furthermore a pair of plasmids was constructed containing the variable Region of GLS-B and GLS-TC, respectively. For cloning of the the hypervariable region, GLS-TC was propagated in CEF and purified by ultracentrifugation. Bursal homogenate of GLS-B was purified by low speed centrifugation and the supernatant was used for the following procedures. After proteinase K (0.5 mg/ml)/sodium dodecylsulphate (SDS, 0.5%) digestion viral RNA was purified, reverse transcribed into cDNA, and amplified by polymerase chain reaction (PCR) following standard procedures using oligonucleotides A14 and A44 (Table 4). Amplification product was cloned blunt ended and plasmids containing appropriate PCR fragments containing plasmids were sequenced. Plasmids containing each an insert of either GLS-TC (pGLS-TC) or GLS-B (pGLS-B) were used in the following experiments. For construction of intergeneric segment A the full length clone pD78A/ΔNB-E/Del was used. pGLS-TC and pGLS-B, respectively, were digested with Sac I and Spe I. Electroeluted fragments were ligated subsequently into previously Sac I-Spe I digested pD78A/ΔNB-E/Del to obtain pD78A/ΔNB-E/Del-GLS-TC and pD78A/ΔNB-E/Del-GLS-B, respectively. Plasmid maps of both plasmids are depicted in FIG. 1B.

Site Directed Mutapenesis

Site directed mutagenesis was performed by PCR. Oligonucleotides contained mutations leading to amino acid exchanges and additional restriction enzyme cleavage sites (Table 4). After PCR amplification using plasmids pAD78/ΔNB, pD78A/ΔNB-E/Del and pD78A-E-661, respectively, fragments were cloned blunt ended and sequenced (pfrag). Clones containing the mutated codons were ligated into previously cut plasmids as follows:

(i) Variant-E IBDV

Figure 1C:
Figure 1D:
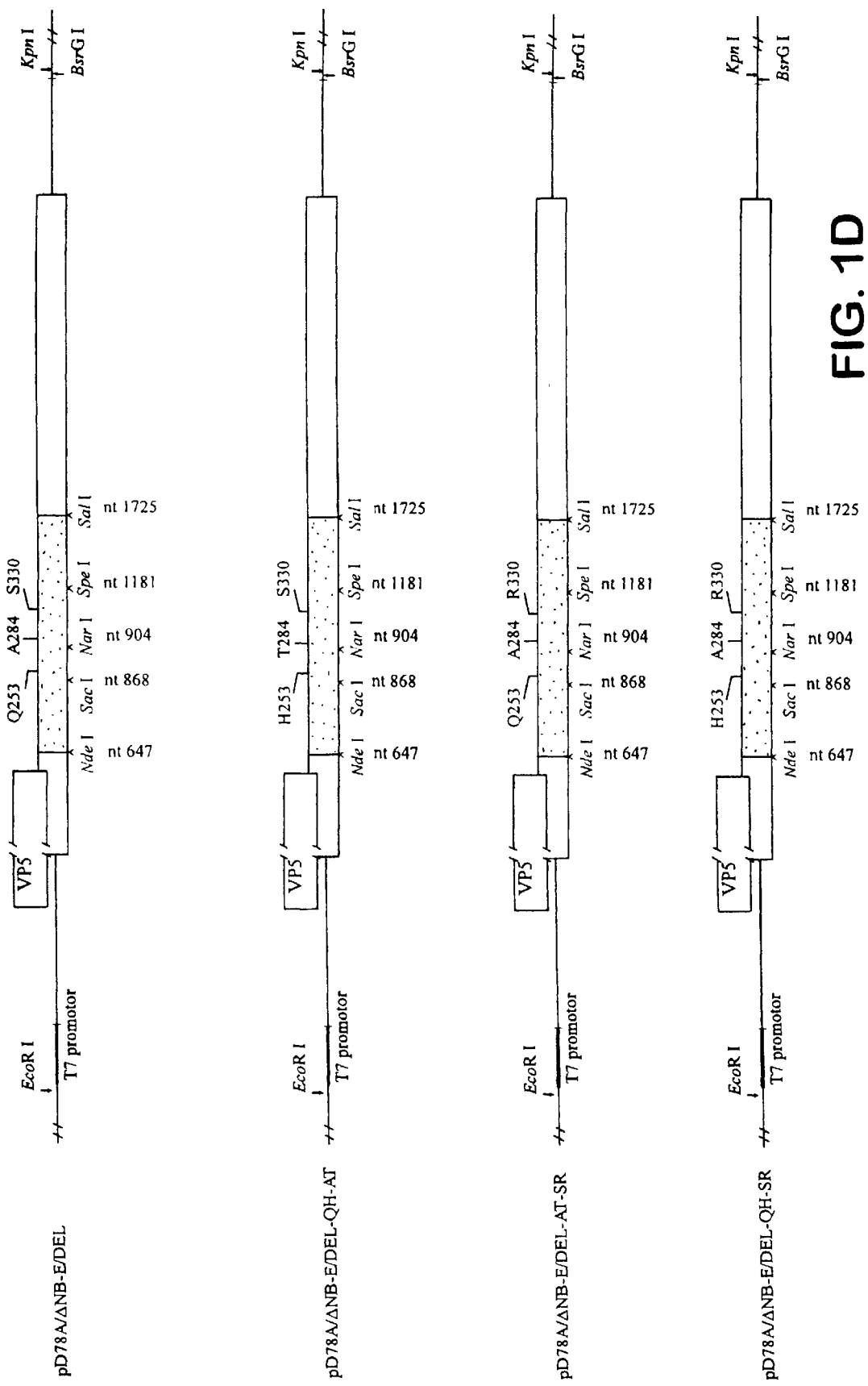
Figure 1E:
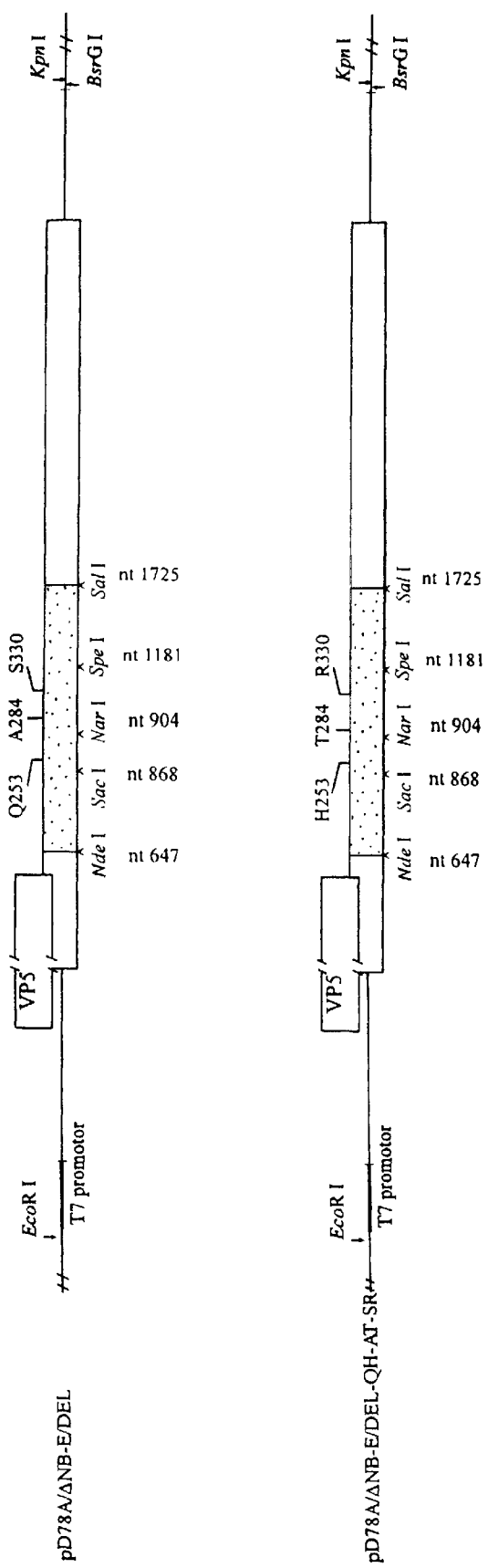

For the establishment of full length clones of segment A of plasmid pD78A/ΔNB-E/Del containing the mutated codons the following PCR fragments were obtained: Primer E/Del-MutQH and A14 (pfragQH), E/Del-MutAT and A14 (pfragAT), E/Del-MutSR and P21F (pfragSR) were used to obtain fragments with the appropriate single amino acid exchanges Q253H, A284T, and S330R, respectively, of the E-Del sequence. PfragQH and pfragSR were Sac I and Spe I cleaved and ligated into previously Sac I-Spe I digested pD78A/ΔNB-E/Del to obtain pD78A/ΔNB-E/DelQH (FIG. 1C) and pD78A/ΔNB-E/DelSR (FIG. 1C), respectively. To construct pD78A/ΔNB-E/DelAT (FIG. 1C) pfragAT was Nar I-Spe I cleaved and subsequently ligated into previously cleaved pD78A/ΔNB-E/Del. To obtain plasmids containing two mutated codons the following PCR were performed: Primer E/Del-MutQH and E/Del-MutSR, and E/Del-MutAT and E/Del-MutSR were used for amplification of fragQH-SR and fragAT-SR on pD78A/ΔNB-E/Del, respectively. After cloning and sequencing pfragQH-SR was Sac I-Spe I digested and subsequently ligated into previously cut pD78A/ΔNB-E/Del to obtain pD78A/ΔNB-E/DelQH-SR (FIG. 1D). For construction of pD78A/ΔNB-E/DelAT-SR (FIG. 1D) plasmid pfragAT-SR was cleaved with Nar I and Spe I and ligated into the identically cleaved pD78A/ΔNB-E/Del. For construction of a plasmid containing mutated codons for two amino acid exchanges (Q253H; A284T) PCR was performed using plasmid pD78A/ΔNB-E/DelAT and primers E/Del-MutQH; A14. Obtained plasmid pfragQH-AT was Sac I-Spe I cleaved and ligated into pD78A/ΔNB-E/Del to obtain pD78A/ΔNB-E/DelQH-AT (FIG. 1D). For cloning of a plasmid containing mutated codons for all three amino acid exchanges (Q253H, A284T, and S330R) primers E/Del-MutQH and E/Del-MutSR were used for amplification of fragQH-AT-SR on pD78A/ΔNB-E/Del-AT. After cleavage of pfragQH-AT-SR with Sac I and Spe I the eluted fragment was ligated into the Sac I and Spe I cleaved pD78A/ΔNB-E/Del to obtain pD78A/ΔNB-E/DelQH-AT-SR (FIG. 1E).

(ii) Classical IBDV

D78

Figure 2:
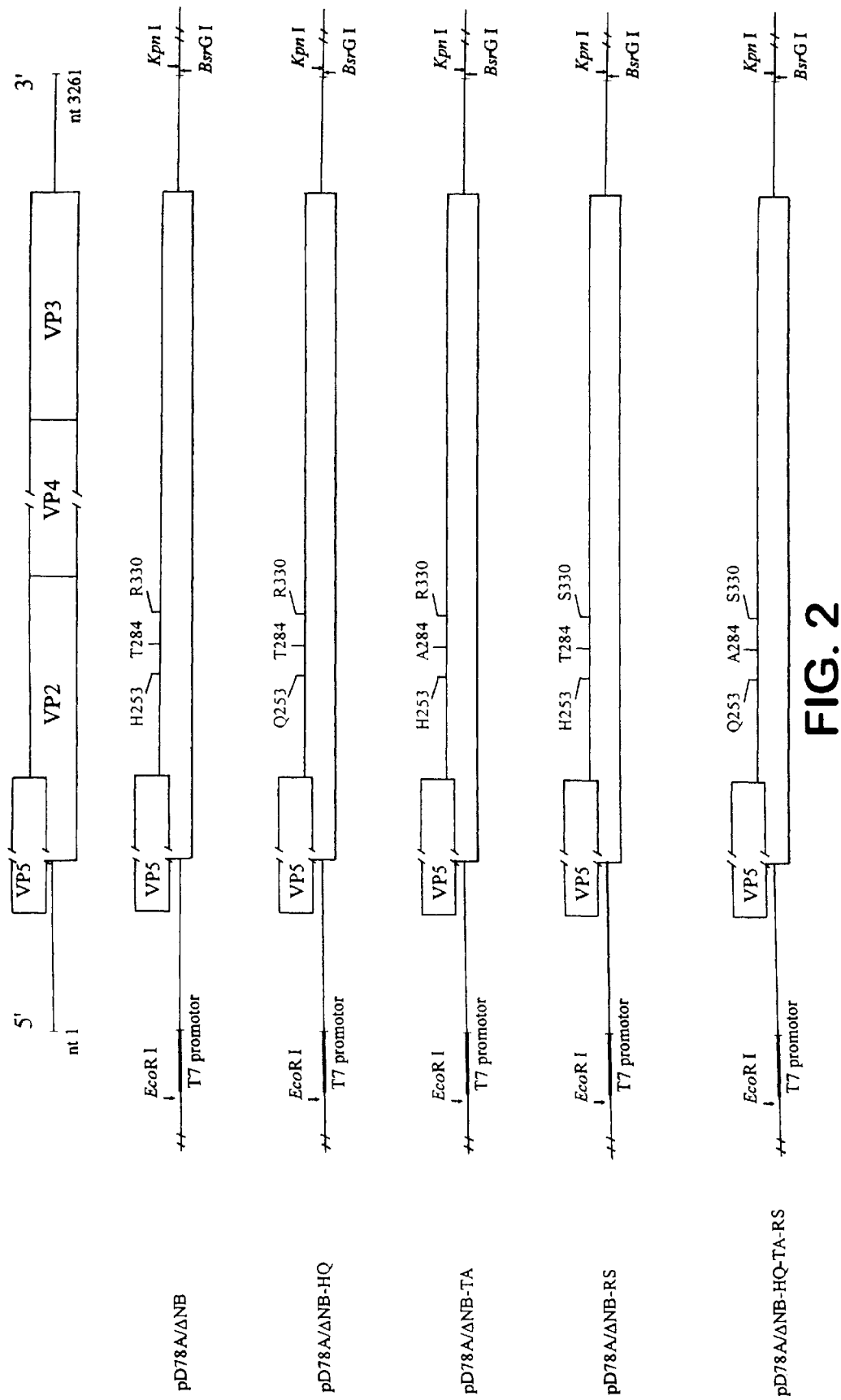

For the establishment of full length clones of segment A of plasmid pD78A/ΔNB containing the mutated codons a Nde I-Hind III fragment of pD78A/ΔNB was subcloned into previously Nde I-Hind III cleaved pUC19 to obtain single restriction enzyme sites for the following procedures (pUC19/NH-D78A). Oligonucleotides D78-MutHQ and A14 (pfragHQ), D78-MutTA and A14 (pfragTA), D78-MutRS and P21F (pfragRS) were used for PCR amplification to obtain fragments with the appropriate single amino acid exchanges H253Q, T284A, and R330S, respectively, of the D78 sequence. Fragment, PfragHQ was cleaved with Sac I and Sty I, pfragTA was cleaved with Nar I and Sty I, pfragRS was cleaved with Sac I and Sty I, and religated into appropriately cleaved pUC19/NH-D78A. Plasmid pUC19/NH-D78A containing the mutated codon was cleaved with Nde I and Sac II, appropriate fragments were electroeluted and ligated into pD78/ΔNB, previously cleaved with Nde I and Sac II, to obtain pD78A/ΔNB-HQ, pD78A/ΔNB-TA, and pD78A/ΔNB-RS, respectively. For the construction of a full length clone containing nucleotide substitutions leading to exchange of all three amino acids (H253Q, A284T, R330S) PCR using oligonucleotides D78-MutHQ, D78-MutRS, and plasmid pD78A/ΔNB-TA was performed. The obtained PCR fragment was cloned blunt ended to obtain pfragHQ-TA-RS. After cleavage of pfragHQ-TA-RS with Sac I and Sty I the electroeluted fragment was cloned into Sac I and Sty I cleaved pUC19/NH-D78A. The obtained plasmid was cleaved with Nde I and Sac II, the appropriate fragment was electroeluted and finally ligated into pD78A/ΔNB, previously cleaved with Nde I and Sac II, to obtain pD78A/ΔNB-HQ-TA-RS. Nucleotide sequences of the obtained mutated plasmids were confirmed by sequencing. Sequences were analyzed with the Wisconsin Package, version 8 (Genetics Computer Group, Madison, Wis.). Plasmids pD78A/ΔNB-HQ, pD78A/ΔNB-TA, pD78A/ΔNB-RS, and pD78A/ΔNB-HQ-TA-RS are depicted in FIG. 2.

priate cleaved pD78A-E-661 to obtain pD78A-E-661-DN-AT.

Furthermore, the nucleotide sequence of amino acid Q253 was exchanged to a nucleotide sequence encoding for H253 by using antisense orientated oligonucleotide Mut 2 (Brown and Skinner, supra; nucleotide no. 874–900, 886–888 is CAT resulting in amino acid substitution O253H). The resulting plasmid pD78A-E-661-QH contained the amino acid exchange Q253H. The exchange of amino acid 284 (A284T) was performed by using antisense orientated oligonucleotide Mut3 (Brown et al., supra, nucleotide no. 966–993, 979–981 is ACC resulting in amino acid substitution A284T) resulting in the plasmid pD78A-E-661-AT. The fourth plasmid pD78A-E-661-QH-AT contained the exchange of both amino acids (Q253H, A284T) by using both oligonucleotides (Mut 2, Mut3) in one site directed mutagenisis reaction. Plasmids p661Apart, pD78A-E-661, pD78A-E-661-DN-AT, pD78A-E-661-QH, pD78A-E-661-AT, and pD78A-E-661-QH-AT are depicted in FIG. 4.

TABLE 4

Oligonucleotides used for the construction of full length cDNA clones of IBDV segment A containing amino acid substitutions[a]

| Designation | Nucleotide sequence | Orientation | Amino acid substitution | Nucleotide no. |
|---|---|---|---|---|
| P21F | CGTCCTAGTAGGGGAAGGGGTC | sense | none | 601–622 |
| | Sac I | | | |
| E/Del-MutQH | GA<u>GAGCTC</u>GTGTTCAAAACAAGCGTCCAtAG | sense | Q 253 H | 861–891 |
| | Nar I | | | |
| E/Del-MutAT | G<u>GGCGCC</u>ACCATCTACCTTATAGGCTTTGATGGGACTGCGGTAATCACCAG AGCTGTGGCCGCAAACAATGGGCTGACGaCCGGCATCGACAATCTTAT | sense | A 284 T | 901–999 |
| | Spe I | | | |
| E/Del-MutSR | CGTAGGCT<u>ACTAGT</u>GTGACGGGACGGAGGGCTCCTGGATAGTTGCCACCAT GGATCGTCACTGCTAGGCTCCCcCgTGCCGACCATGACATCTGTTCCCC | antisense | S 330 R | 1094–1193 |
| | Sac I | | | |
| D78-MutHQ | GA<u>GAGCTC</u>GTGTTTCAAAACAAGCGTCCAaGG | sense | H 253 Q | 861–891 |
| | Nar I | | | |
| D78-MutTA | G<u>GGCGCC</u>ACCATCTACCTCATAGGCTTTGATGGGACAACGGTAATCACCAG GGCTGTGGCCGCAAACAATGGGCTGACGgCCGGCACCGACAACCTTATG | sense | T 284 A | 901–1000 |
| | Sty I | | | |
| D78Mut-RS | CGGAGGGCCCCTGGATAGTTGCCA<u>CCATGG</u>ATCGTCACTGCTAGGCTCCCaC TTGC | antisense | R 330 S | 1115–1170 |
| A44 | CAAGCCTCAGCGTTGGGGGAGAGC | sense | none | 833–866 |
| A14 | GATCAGCTCGAAGTTGCTCACCCCA | antisense | none | 1228–1252 |

[a]Composition and location of the oligonucleotide primers used for site directed mutagenisis and cloning. The used restriction sites ae underlined and appropriate restriction enzymes are named. Changed nucleotides for mutagenisis are in small letter code and the coding nucleotide triplett are marked in boldface type. The positions were the primers bind (nucleoide number) and the numbering of the amino acides are in according to the published sequence of P2 strain (Mundt and Müller, 1995, supra; NCBI accession number X 84034).

UK661

For site directed mutagenesis plasmid pD78A-E-UK661 were EcoR I/Kpn I cleaved and full lenght sequence of the segment A containing fragment was subsequentely ligated into the EcoR I/Kpn I cleaved plasmid vector pBS⁻ (Stratgene). Resulting plasmid pBSD78A-E-661 was used for site directed mutagenesis experiments following the method as described earlier (Kunkel et al., Methods Enzymol. 154, 367–382, 1987). Based on the results of Lim et al. (1999, supra) the nucleotide sequence for amino acid 279 and 284 of the plasmid pBSD78A-E-661 were exchanged (D279N, A284T) using antisense orientated oligonucleotide Mut1 (Brown and Skinner, supra; nucleotide no. 947–1001, 946–966 is AAC and 979–981 is ACG resulting in amino acid substitution D279N and A284T). The appropriate part of the resulting plasmid pBSD78A-E-661-DN-AT was sequenced. After Nde I/Spe I cleaveage of pBSD78A-E-661-DN-AT the 535 bp fragment was ligated into the appro- Contruction of a Full Length cDNA Clone of Segment B Strain D78

Figure 3:
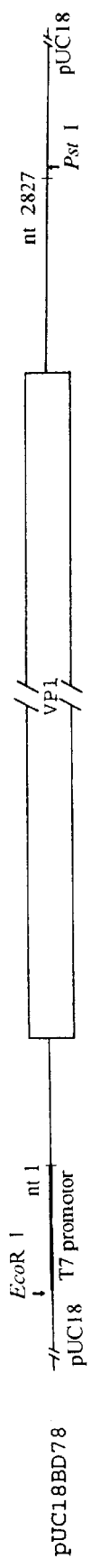

For cloning of the full length cDNA of segment B of serotype I strain D78, virus was propagated in CEF and purified by ultracentrifugation. Genomic viral RNA of strain D78 was purified, reverse transcribed into cDNA, and amplified by polymerase chain reaction (PCR) following standard procedures using oligonucleotides as described (Mundt and Vakharia, 1996). Amplification product was cloned blunt ended and plasmids containing appropriate PCR fragments were sequenced. The cloning procedure to obtain a plasmid containing the full length cDNA of segment B (pUC18BD78) under control of the T7-RNA polymerase promotor corresponded to the procedure described by Mundt and Vakharia (1996, supra) for segment B of strain P2 (FIG. 3).

Strain UK661

Figure 5:
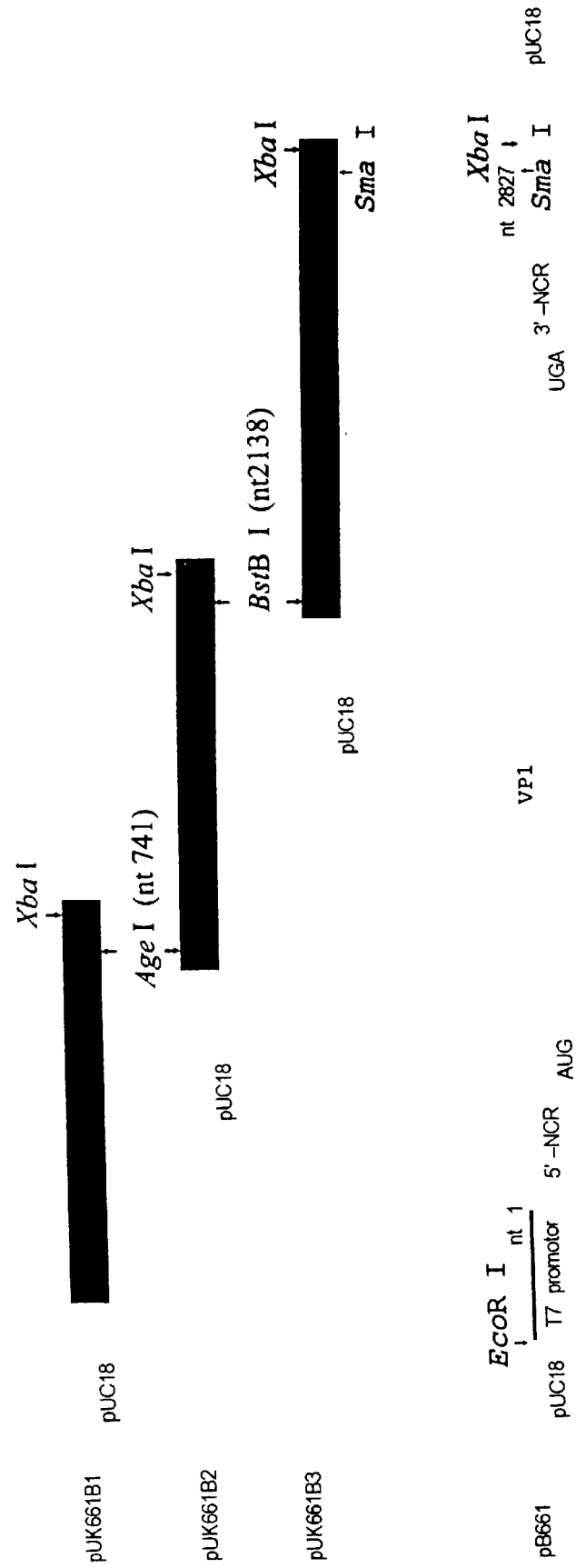

Three pairs of oligonucleotides derived from the sequence information in Brown and Skinner (1996, supra) were used:

i) UK661BFor1 (sequence in accordance to the oligonucleotide B5'-P2, Mundt and Vakharia, 1996, supra), antisense orientated UK661BRev1 (nucleotide no. 708–736). The 5'-end of oligonucleotide UK661BRev1 contains additional to the sequence of segment B of strain UK-661 the restriction enzyme cleavage site Xba I containing nonasequence 5'-CTCTAGAGG.;

ii) UK661BFor2 (nucleotide no. 751–677), antisense orientated UK661BRev2 (nucleotide no. 2089–2113). The 5'-end of oligonucleotide UK661BRev2 contains additional to the sequence of segment B of strain UK-661 the restriction enzyme cleavage site Xba I containing nonasequence 5'-CTCTAGAGG.

iii) UK661BFor3 (nucleotide no. 2011–2035), antisense orientated UK661BRev3 (Mundt and Müller, 1995, supra, nucleotide no. 2804–2827). The 5'-end of oligonucleotide UK661BRev3 contains additional to the sequence of segment B of strain UK-661 the restriction enzyme cleavage sites Xba I containing nonasequence 5'-TCTAGAGCCC. There, the triplet CCC created a Sma I cleavage site together with the last three nucleotides of the viral genomic sequence of segment B (nucleotide no. 2825–2827). By using these three pairs of oligonucleotides UK661BFor1; UK661BRev1, UK661BFor2; UK661BRev2, and UK661BFor3; UK661BRev3 during RT-PCR three cDNA fragments were amplified and cloned blunt ended into the Sma I cleaved Vector pUC18 to obtain pUK661B1, pUK661B2, and pUK661B3, respectively. After sequencing of the three inserted fragments pUK661B2 was cleaved with Age I and Xba I to obtain a 1441 bp fragment which was subsequently ligated into the Age I/Xba I cleaved pUK661B1 to obtain pUK661B12. For construction of the full length cDNA clone of segment B pUK661B3 was BstB I/Xba I cleaved and the obtained 694 bp fragment was ligated into the BstB I/Xba I cleaved pUK661B12. The resulting plasmid pB661 contained the full length cDNA sequence of segment B of strain UK661 under control of the T7 promoter. pB661 is depicted in FIG. 5 (the numbering is in accordance with the sequence of the P2 strain in Mundt and Müller, 1995, supra).

Virus Recovery from cRNA in Tissue Culture

For in vitro transcription of RNA plasmids pAD78/ΔNB, pAD78/ΔNB-HQ, pAD78/ΔNB-TA, pAD78/ΔNB-RS, pAD78/ΔNB-HQ-TA-RS, pD78A/ΔNB-E/Del, pD78A/ΔNB-E/Del-QH, pD78A/ΔNB-E/Del-AT, pD78A/ΔNB-E/Del-SR, pD78A/ΔNB-E/Del-QH-AT, pD78A/ΔNB-E/Del-AT-SR, pD78A/ΔNB-E/Del-QH-SR, pD78A/ΔNB-E/Del-QH-AT-SR and pD78B were linearized by cleavage with either BsrGI or Pst I. Further treatment of linearized DNA and transcription were carried out as described by Mundt and Vakharia (1996), with two exceptions: i) the transcription mixtures were not phenol/chloroform purified, and ii) QM-7 cells were used for transfection experiments. Two days after transfection cells were freeze/thawed, centrifuged at 700×g to eliminate cellular debris, and the resulting supernatants were further clarified by filtration through 0.45 μm filters and stored at −70° C. For immunofluorescence studies QM-7 cells were grown on sterile cover slips.

For in vitro transcription of RNA plasmids containing UK661 segment A (FIG. 5) were linearized by cleavage with BsrGI. Segment B of strain D78 was linearized with Pst I whereas segment B of srain UK661 was linearized with Sma I. Further treatment of linearized DNA and transcription were carried out as described above.

Detection of IBDV Antigen

IBDV antigen was detected by indirect immunofluorescence assay (IFA) and Western blot using rabbit anti-IBDV antiserum. For IFA CEF grown on cover slips were incubated with supernatants of transfected QM-7, CEF, and CAM, respectively, used for passaging. After an incubation time of 16 hours CEF were acetone fixed and processed for IFA. For examination of IBDV replication after transfection QM-7 cells grown on cover slips were incubated for 24 hours or 48 hours, acetone fixed, and processed for IFA.

Results

Transfection Experiments with Intergeneric cRNA

For transfection experiments a full length cDNA clone of segment A of strain D78 (pD78A/ΔNB) and intergeneric segment A pD78A/ΔNB-E/Del were transcribed into synthetic cRNA and cotransfected with segment B (pD78B) full length cRNA into QM-7 cells as well as CEF in parallel. Two days after transfection cells were freeze/thawed and the resulting supernatants were passaged two times on CEF. CEF were incubated up to five days after infection in each passage. After freeze/thawing each transfection supernatant as well as each passage of each transfection were tested for IBDV antigen by IFA using CEF. Transfection experiments were repeated three times. Virus was generated after transfection of cRNA from plasmid pD78B in combination with pAD78/ΔNB leading to generation of strain D78r. In contrast, after transfection experiments using cRNA from pD78A/ΔNB-E/Del and pD78B no tissue culture infecting virus could be isolated. In order to analyze whether transfection was followed by replication, transfection was carried out using QM-7 cels growing on cover slips. Here in both cases virus antigen was detected 24 hours after transfection using IFA. Thus we proved that viral replication occurred in both cases but only in the case of D78r it was possible to generate tissue culture infecting IBDV.

Transfection Experiments with Mutated cRNA

Based on the results of the sequence comparison a number of different mutated full length cDNA clones was established by site directed mutagenesis.

(i) Variant-E IBDV

Mutated plasmids of pD78A/ΔNB-E/Del were generated containing aa acid substitutions at positions 253, 284, and 330 in all possible seven combinations (Table 5). Transfection experiments and passaging were performed three times in parallel on CEF and QM-7 cells. The obtained supernatants were analyzed for infectivity by IFA. After transfection of cRNA of plasmids pD78A/ΔNB-E/Del, pD78A/ΔNB-E/Del-QH, pD78A/ΔNB-E/Del-AT, pD78A/ΔNB-E/Del-SR, pD78A/ΔNB-E/Del-AT-SR, and pD78A/ΔNB-E/Del-QH-SR in combination with cRNA of pD78B QM-7 cells or CEF infecting virus could not be isolated. Transfection of cRNA obtained from pD78A/ΔNB-E/Del-QH-AT or pD78A/ΔNB-E/Del-QH-AT-SR led to generation of infectious virus (D78A-E/Del-QH-AT and D78A-E/Del-QH-AT-SR). Specificity was confirmed by IFA on CEF as well as QM-7 cells. This indicated that VP2 of IBDV plays a critical role in tissue culture infection. Aa substitutions (BU) Q-253-H (TC) and (BU) A-284-T (TC) were necessary and sufficient to generate IBDV infectious for the tissue cultures used. The IBDV mutant having the three Aa substitutions (D78/Variant-E CEF adapted) was used for further examination (Example 2).

(ii) Classical IBDV

D78

To confirm these results a second set of plasmids was constructed using pAD78/ΔNB for site directed mutagenesis to obtain plasmids with either substitution of a single aa (pAD78/ΔNB-HQ, pAD78/ΔNB-TA, pAD78/ΔNB-RS) or of all three aa (pAD78/ΔNB-HQ-TA-RS). These four plasmids were used for transfection experiments in combination with pD78B as described above. Infectious IBDV could be generated after transfection of cRNA from pAD78/ΔNB-RS as detected by IFA. Again, aa 330 did not have any influence on the ability of the generated virus to infect tissue culture.

All constructs were tested for replication after transfection by IFA. IBDV antigen could be detected specifically 24 hours and 48 hours after transfection, showing typical large intensely stained aggregates within the cytoplasm.

UK661

For transfection experiments a full length cDNA clone of chimeric segments A pD78A-E-661, pD78A-E-661-DN-AT, pD78A-E-661-QH, pD78A-E-661-AT, and pD78A-E-661-QH-AT were transcribed into synthetic cRNA and cotransfected with either segment B of strain D78 or segment B of strain UK661 full length cRNA into QM-7 cells as well as into CEC in parallel. Two days after transfection cells were freeze/thawed and the resulting supernatants were passaged once on CEC. CEC were incubated 24 or 48 hours after infection, fixed and processed for immunofluorescence. Virus infectious for CEC was generated after transfection of cRNA from plasmid pD78A-E-661-QH-AT in combination with both, pD78B and pB661 leading to the chimeric IBDV D78A-E-661-QH-AT. In contrast, after transfection experiments using cRNA from pD78A-E-661, pD78A-E-661-DN-AT, pD78A-E-661 -QH, pD78A-E-661-AT in combination with cRNA from either pBD78 or pB661 no tissue culture infecting virus could be isolated. Upon incubating the transfection supernatant 72 hours after infection single infected CEF are detectable in the case of D78-E-661-DN-AT.

(iii) GLS IBDV

To confirm the results of the transfection experiments using intergeneric as well as mutated plasmids we took advantage of a naturally occuring pair of IBDV strains. The variable region of VP2 of the bursal derived GLS strain (GLS-B) and the tissue culture adapted variant GLS-TC were amplified, cloned and analyzed. Comparison of the amino acid sequences of the two GLS-strains obtained from pGLS-B and pGLS-TC, respectively, revealed one amino acid exchange at position 284 [(GLS-B) A→T (GLS-TC)] between both sequences (FIG. 1B). Aa 253 (Q) and 330 (S) were identical to the aa of the BU group as described above. To analyze if the exchange at position 284 (A→T ) was sufficient for generation of infectious virus two plasmids (pD78A/ΔNB-E/Del-GLS-TC and pD78A/ΔNB-E/Del-GLS-B) containing the hypervariable region of VP2 of the both GLS variants were consructed. cRNA of pD78A/ΔNB-E/Del-GLS-TC and pD78A/ΔNB-E/Del-GLS-B, respectively, were transfected in parallel combined with cRNA of pD78B into QM-7 cells as well as CEF. After passaging of the supernatants in tissue culture infectious virus could be detected by IFA as well as CPE after transfection of cRNA of pD78A/ΔNB-E/Del-GLS-TC. In several attempts transfection of cRNA from pD78A/ΔNB-E/Del-GLS-B failed to produce supernatants containing tissue culture infectious IBDV. In vitro transcription/translation of both plasmids pD78A/ΔNB-E/Del-GLS-TC and pD78A/ΔNB-E/Del-GLSB showed complete processing of the polyproteins. After transfection of cRNA of both plasmids together with cRNA from pD78B viral antigen was detected by IFA. Thus both chimeras proved to be replication-competent. Taken together here the exchange of the hypervariable region of VP2 leading to a single aa exchange at position 284 was sufficient to generate infectious intergeneric IBDV.

TABLE 5

Summary of intergeneric full length cDNA clones of IBDV segment A containing amino acid substitutions

| Plasmid[a] | aa[b] 253 | aa · 284 | aa · 330 | Tissue culture Transfection[c] | Passage[d] |
|---|---|---|---|---|---|
| pD78A/ΔNB-E/Del | Q | A | S | + | − |
| pD78A/ΔNB-E/Del-QH | H | A | S | + | − |
| pD78A/ΔNB-E/Del-AT | Q | T | S | + | − |
| pD78A/ΔNB-E/Del-SR | Q | A | R | + | − |
| pD78A/ΔNB-E/Del-QH-AT | H | T | S | + | + |
| pD78A/ΔNB-E/Del-AT-SR | Q | T | R | + | − |
| pD78A/ΔNB-E/Del-QH-SR | H | A | R | + | − |
| pD78A/ΔNB-E/Del-QH-AT-SR | H | T | R | + | + |
| pD78A/ΔNB | H | T | R | + | + |
| pD78A/ΔNB-HQ | Q | T | R | + | − |
| pD78A/ΔNB-TA | H | A | R | + | − |
| pD78A/ΔNB-RS | H | T | S | + | + |
| pD78A/ΔNB-HQ-TA-RS | Q | A | S | + | − |
| pD78A/ΔNB-E/Del-GLS-TC | Q | T | S | + | + |
| pD78A/ΔNB-E/Del-GLS-BU | Q | A | S | + | − |

[a]Plasmids are based on the full length cDNA clone of segment A of tissue culture adapted serotype I strain D78. Sequences of bursal derived serotype I strains GLS-BU, Delaware E (E/Del) and of the tissue culture adapted serotype I strain GLS-TC were substituted with D78 sequences.
[b]The numbering of the amino acids (aa) according to the published sequence of P2 strain (Mundt and Müller, 1995, supra; NCBI accession number X 84034). Naturally occuring amino acids are typed italics and changed amino acids are marked in boldface type.
[c]Chicken embryo cells (CEF) as well as QM- 7 cells were used for transfection experiments. IBDV antigen was detected by indirect immunofluorescence using rabbit anti-IBDV serum (Mundt et al., 1995) 24 hours after transfection. antigen positive (+), antigen negative (−)
[d]CEF were used for passaging of transfection supernatants. IBDV antigen was detected by indirect immunofluorescence using rabbit anti- IBDV serum (Mundt et al., 1995; supra) after passage onto CEF. antigen positive (+), antigen negative (−)

Example 2

Biological Properties of CEF Adapted Variant-E IBDV Mutant

Materials and Methods
Preparation of IBDV Vaccines
Chimeric D78/Variant-E (Bursa Adapted)

9–12 days old SPF eggs were infected with chimeric D78/Variant-E/D78 (D78/variant-E/D78 without 3 amino acid exchanges at Q253H, A284T, and S330R) via the dropped chorion allantoic membrane (CAM) route. Five days after infection the CAM and embryos were harvested and homogenized. The homogenate was titrated on CAM. The supernatant was diluted to result in a vaccine dose of $10^{2.0}$ EID$_{50}$/animal for the application via the eye-drop route.

Chimeric D78/Variant-E (CEF Adapted)

Primary chicken embryo fibroblasts (CEF) cells were prepared at a final concentration of $2\times10^6$/ml. The cells were cultured in Eagles minimum essential medium containing 5% fetal calf serum. To 15 ml of this cell suspension 0.1 ml IBDV (D78/variant-E/D78 with 3 amino acid exchanges at Q253H, A284T, and S330R) virus which was dissolved in 1 ml, was added. After incubation for 3–6 days in a high humidity incubator at 37° C., the supernatant was diluted to result in a vaccine dose of $10^{5.3}$ or $10^{3.5}$ TCID$_{50}$/animal for the application routes eye-drop or intramuscular injection, respectively.

Commercial Available Classical IBDV Vaccine Nobilis Strain D78

The vaccine was diluted to result in a vaccine dose of $10^{3.3}$ TCID$_{50}$/animal for the application routes eye-drop route.

Identification of IBDV Vaccines by Means of Panel Test

Both IBDV-strains were identified by means of ELISA using different monoclonal antibodies according to Van Loon et al (Van Loon, A. A. W. M., D. Lütticken and D. B. Snyder. Rapid quantification of infectious bursal disease (IBD) challenge, field or vaccine virus strains. International symposium on infectious bursal disease and chicken infectious anemia, Rauischhilzhausen, Germany, 179–187, 1994).

Growth on CEF

Both IBDV-strains were used to infected CEF. The induction of specific CPE (cytopathic effect) for IBDV was microscopically examined for a period of 6 days.

Vaccination

The effect of the different vaccines is assessed by measurement of the resistance to challenge obtained from administering a challenge virus (virulent IBDV strain variant-E), 14 days after vaccination. The chimeric vaccine D78/Variant-E (bursa adapted), $10^{2.0}$ EID$_{50}$/animal, was applied via the eye-drop route at 2 weeks of age. The chimeric vaccine D78/Variant-E (CEF adapted), $10^{5.5}$ or $10^{3.5}$ TCID$_{50}$/animal, was applied via the eye-drop route or via intramuscular injection at 2 weeks of age, respectively. The commercial available classical vaccine Nobilis strain D78 (Intervet International B.V., the Netherlands), $10^{3.3}$ TCID$_{50}$/animal was applied via the eye-drop route at 2 weeks of age. Presence of IBDV in the bursa of Fabricius and microscopic lesions in the bursa of 5 animals per group were investigated, 3, 7, 10 and 13 days after vaccination and 3 days after challenge. Protection against challenge was determined.

Results
Identification of IBDV Vaccines by Means of Panel Test

As can be seen in Table 6, chimeric D78/Variant-E (bursa adapted) and chimeric D78/Variant-E (CEF adapted) have an identical reaction pattern with the different MCA. This means that the 3 amino acid changes have no influence on the epitopes present on the virus as determined by the different MCA. The classical commercial vaccine has a different reaction pattern with the different MCA.

TABLE 6

Panel pattern of different IBDV viruses with different MCA.
+ epitope present on virus, − epitope not present on virus.

| | MCA | | | | | | |
|---|---|---|---|---|---|---|---|
| Virus | B29 | 8 | R63 | BK9 | 67 | 57 | B69 |
| Chimeric D78/Variant-E (bursa) | + | + | + | + | + | − | − |
| Chimeric D78/Variant-E (CEF) | + | + | + | + | + | − | − |
| Nobilis strain D78 | + | + | + | − | − | − | + |
| Control IBDV strains: | | | | | | | |
| Classical | + | + | + | − | − | − | + |
| Variant-E | + | + | + | + | + | − | − |
| GLS | + | + | − | − | − | + | − |

Growth on CEF

As can be seen in Table 7, chimeric D78/Variant-E (bursa) is not able to grow on CEF. The chimeric D78/Variant-E (CEF) and the classical commercial vaccine Nobilis strain D78 are both able to replicate on CEF inducing a CPE.

TABLE 7

Ability to grow on CEF and inducing specific IBDV-CPE. + = does induce CPE on CEF; − = does not cause CPE on CEF.

| Virus | CEF growth |
|---|---|
| Chimeric D78/Variant-E (bursa) | − |
| Chimeric D78/Variant-E (CEF) | + |
| Nobilis strain D78 | + |

Average microscopic lesion score in the bursa 3, 7, 10 and 13 days after vaccination and 3 and 10 days after challenge. Results are depicted in Table 8. As can be seen from Table 3, the none-CEF adapted strain chimeric D78/Variant-E (bursa) is virulent and induces complete lymphocytic depletion, already 7 days after vaccination. In contrast the tissue culture adapted strain D78/Variant-E (CEF) does not induce lesions after vaccination. The commercial vaccine induces mild to moderate lesions after vaccination. Individual data showed that animals vaccinated with chimeric D78/Variant-E (bursa) or D78 were protected against challenge. Animals vaccinated with D78/Variant-E via the ocular or intramuscular route also resulted in a protection 3 days after challenge, although less than that induced by the virulent parent strain.

TABLE 8

Average bursal lesion score

| | Days after vaccination | | | | Days after challenge | |
|---|---|---|---|---|---|---|
| Virus | 3 | 7 | 10 | 13 | 3 | 10 |
| D78/variant-E/D78 | 3.2 | 5.0 | 5.0 | 5.0 | 4.4C | 4.7 |
| D98/VP5+ (oc) | 0 | 0 | 0 | 0 | 3.0A | 4.1 |
| D98/VP5+ (im) | 0 | 0 | 0 | 0 | 1.0A | 2.8 |
| Nobilis strain D78 | 0.2 | 2.2 | 2.0 | 1.8 | 2.8C | 1.9 |
| None vaccinated controls | | | | | 5.0A | |

(oc) = ocular route;
(im) = intramuscular route;
C = chronic lesions;
A = acute lesions

What is claimed is:

1. A genetically engineered, infectious IBDV mutant capable of replication in CEF cell culture, comprising codons for amino acids 253 (His) and 284 (Thr), and optionally 330 (Arg) in the VP2 gene of Classical or Variant-E IBDV, or a codon for amino acid 284 (Thr) in the VP2 gene of a GLS IBDV.

2. A genetically engineered, infectious IBDV mutant according to claim 2, wherein it is a chimeric IBDV mutant.

3. A genetically engineered, infectious IBDV mutant according to claim 2, wherein it is D78/Variant-E.

4. A vaccine for use in the protection of poultry against disease resulting from IBDV infection, comprising a genetically engineered IBDV mutant capable of replication in CEF cell culture comprising a mutation in (a) one or more codons of the VP2 gene encoding an amino acid at positions 253 and 284 of a Variant-E or Classical IBDV strain, or in
   (b) a codon of the VP2 gene encoding an amino acid at position 284 of a GLS IBDV strain,
   wherein the codons of the VP2 gene encoding amino acids at positions 253 and 284 encode a histidine and threonine, respectively, in the case of a Variant-E or Classical IBDV strain, or wherein, the codon encoding the amino acid at position 284 of the mutated VP2 gene encodes a threonine in the case of a GLS IBDV strain together with a pharmaceutical carrier or diluent.

5. The vaccine of claim 4, wherein the IBDV mutant further comprises a serine, arginine or lysine residue at position 330 of the VP2 protein.

6. An infectious IBDV mutant that will replicate in CEF cell culture and that comprises one or more genetically engineered codons, such that the IBDV comprises codons for amino acids 253 (His) and 284 (Thr), and optionally 330 (Arg) in the VP2 gene of Classical or Variant-E IBDV, or a codon for amino acid 284 (Thr) in the VP2 gene of a GLS IBDV.

7. A genetically engineered, infectious IBDV mutant according to claim 6, wherein IBDV mutant is selected from the group consisting of a chimeric IBDV mutant and a 78/Variant-E.

8. The vaccine of claim 4, further comprising an adjuvant.

9. The vaccine of claim 4 wherein the mutant is either a live attenuated or an inactivated mutant.

* * * * *